United States Patent
Kellar

(10) Patent No.: US 9,005,306 B2
(45) Date of Patent: *Apr. 14, 2015

(54) MEDICAL IMPLANTS WITH COMPLIANT WEAR-RESISTANT SURFACES

(75) Inventor: Franz W. Kellar, Gastonia, NC (US)

(73) Assignee: Biomedflex, LLC, Gastonia, NC (US)

( * ) Notice: Subject to any disclaimer, the term of this patent is extended or adjusted under 35 U.S.C. 154(b) by 390 days.

This patent is subject to a terminal disclaimer.

(21) Appl. No.: 11/936,601

(22) Filed: Nov. 7, 2007

(65) Prior Publication Data

US 2008/0154369 A1 Jun. 26, 2008

Related U.S. Application Data

(60) Provisional application No. 60/864,667, filed on Nov. 7, 2006.

(51) Int. Cl.
*A61F 2/30* (2006.01)
*A61F 2/44* (2006.01)
(Continued)

(52) U.S. Cl.
CPC .............. *A61F 2/30767* (2013.01); *A61F 2/32* (2013.01); *A61F 2/34* (2013.01); *A61F 2/36* (2013.01); *A61F 2/367* (2013.01); *A61F 2/3676* (2013.01); *A61F 2/38* (2013.01); *A61F 2/3859* (2013.01); *A61F 2/389* (2013.01); *A61F 2002/30014* (2013.01); *A61F 2002/30112* (2013.01); *A61F 2002/30153* (2013.01);
(Continued)

(58) Field of Classification Search
CPC ... A61F 2/32; A61F 2/38; A61F 2002/30014; A61F 2002/30018

USPC ............ 623/18.11, 19.11–19.13, 2.11, 623/22.13–22.21, 22.3, 23.4, 16.11, 17.14, 623/19.12, 20.14, 20.22–20.23, 21.13, 623/21.16–21.17, 22.11, 22.13–22.18, 623/22.21–22.22, 22.24–22.26, 623/23.11–23.13, 23.39–23.43

See application file for complete search history.

(56) References Cited

U.S. PATENT DOCUMENTS 3,521,302 A 7/1970 Muller
3,723,995 A 4/1973 Baumann
(Continued)

FOREIGN PATENT DOCUMENTS

DE 4102509 7/1992
DE 4423020 1/1996
(Continued)

OTHER PUBLICATIONS

Alvarado et al. "Biomechanics of Hip and Knee Prostheses". Applications of Engineering Mechanics in Medicine, GED—University of Puerto Rico Mayaguez (2003): 1-20.*

(Continued)

*Primary Examiner* — Andrew Iwamaye
(74) *Attorney, Agent, or Firm* — Trego, Hines & Ladenheim, PLLC

(57) ABSTRACT

A medical implant includes a first member adapted to be implanted to bond and having a substantially rigid first contact surface; and a second member adapted to be implanted to bone and having a substantially rigid second contact surface which bears against the first contact surface so as to transfer load from one member to the other while allowing relative motion between the two members; At least one of the first and second contact surfaces is adapted to have resilient properties when placed under load.

5 Claims, 16 Drawing Sheets

(51) Int. Cl.
- *A61F 2/32* (2006.01)
- *A61F 2/38* (2006.01)
- *C23C 30/00* (2006.01)
- *A61F 2/34* (2006.01)
- *A61F 2/36* (2006.01)

(52) U.S. Cl.
CPC ........... *A61F 2002/30322* (2013.01); *A61F 2002/30324* (2013.01); *A61F 2002/30589* (2013.01); *A61F 2002/3066* (2013.01); *A61F 2002/30673* (2013.01); *A61F 2002/30675* (2013.01); *A61F 2002/30682* (2013.01); *A61F 2002/30878* (2013.01); *A61F 2002/3092* (2013.01); *A61F 2002/30922* (2013.01); *A61F 2002/30929* (2013.01); *A61F 2002/30934* (2013.01); *A61F 2002/30937* (2013.01); *A61F 2002/30955* (2013.01); *A61F 2002/30968* (2013.01); *A61F 2002/30981* (2013.01); *A61F 2002/3446* (2013.01); *A61F 2002/3495* (2013.01); *A61F 2002/3611* (2013.01); *A61F 2002/3895* (2013.01); *A61F 2230/0004* (2013.01); *A61F 2230/0019* (2013.01); *A61F 2250/0018* (2013.01); *A61F 2250/0026* (2013.01); *A61F 2250/0036* (2013.01); *A61F 2310/00011* (2013.01); *A61F 2310/00179* (2013.01); *A61F 2310/00239* (2013.01); *A61F 2310/0058* (2013.01); *C23C 30/00* (2013.01)

(56) References Cited

U.S. PATENT DOCUMENTS

| | | |
|---|---|---|
| 3,744,061 A | 7/1973 | Frost |
| 3,842,442 A | 10/1974 | Kolbel |
| 3,945,739 A | 3/1976 | Abe |
| 4,031,570 A * | 6/1977 | Frey ........................... 623/22.39 |
| 4,044,403 A | 8/1977 | D'Errico |
| 4,159,544 A | 7/1979 | Termanini |
| 4,224,696 A | 9/1980 | Murray et al. |
| 4,309,778 A | 1/1982 | Buechel et al. |
| 4,437,193 A | 3/1984 | Oh |
| 4,550,450 A | 11/1985 | Kinnett |
| 4,568,348 A | 2/1986 | Johnson et al. |
| 4,673,408 A | 6/1987 | Grobbelaar |
| 4,718,911 A | 1/1988 | Kenna |
| 4,759,766 A | 7/1988 | Buettner-Janz et al. |
| 4,795,469 A | 1/1989 | Oh |
| 4,813,961 A | 3/1989 | Sostegni |
| 4,878,918 A | 11/1989 | Tari et al. |
| 4,904,106 A | 2/1990 | Love |
| 4,955,919 A | 9/1990 | Pappas et al. |
| 4,964,865 A | 10/1990 | Burkhead et al. |
| 4,997,432 A | 3/1991 | Keller |
| 5,061,288 A | 10/1991 | Berggren et al. |
| 5,062,853 A | 11/1991 | Forte |
| 5,080,675 A | 1/1992 | Lawes et al. |
| 5,080,678 A * | 1/1992 | Spotorno et al. ........... 623/22.14 |
| 5,092,898 A * | 3/1992 | Bekki et al. ................ 623/22.16 |
| 5,116,375 A | 5/1992 | Hofmann |
| 5,116,376 A | 5/1992 | May |
| 5,181,926 A * | 1/1993 | Koch et al. ................. 623/22.14 |
| 5,197,987 A * | 3/1993 | Koch et al. ................. 623/20.28 |
| 5,358,530 A | 10/1994 | Hodorek |
| 5,389,107 A * | 2/1995 | Nassar et al. .............. 623/23.17 |
| 5,405,394 A | 4/1995 | Davidson |
| 5,413,604 A | 5/1995 | Hodge |
| 5,462,362 A * | 10/1995 | Yuhta et al. ..................... 384/13 |
| 5,480,442 A | 1/1996 | Bertagnoli |
| 5,480,446 A | 1/1996 | Goodfellow et al. |
| 5,507,816 A | 4/1996 | Bullivant |
| 5,549,693 A | 8/1996 | Roux et al. |
| 5,549,695 A | 8/1996 | Spotorno et al. |
| 5,549,697 A | 8/1996 | Caldarise |
| 5,549,699 A | 8/1996 | MacMahon et al. |
| 5,549,700 A | 8/1996 | Graham et al. |
| 5,593,445 A * | 1/1997 | Waits ........................... 623/23.42 |
| 5,609,645 A | 3/1997 | Vinciguerra |
| 5,641,323 A | 6/1997 | Caldarise |
| 5,674,296 A | 10/1997 | Bryan et al. |
| 5,676,701 A | 10/1997 | Yuan et al. |
| 5,702,456 A | 12/1997 | Pienkowski |
| 5,702,470 A | 12/1997 | Menon |
| 5,725,584 A | 3/1998 | Walker et al. |
| 5,782,927 A | 7/1998 | Klawitter et al. |
| 5,800,555 A | 9/1998 | Gray et al. |
| 5,824,101 A | 10/1998 | Pappas |
| 5,871,542 A | 2/1999 | Goodfellow et al. |
| 5,871,546 A | 2/1999 | Colleran et al. |
| 5,879,404 A * | 3/1999 | Bateman et al. ........... 623/22.21 |
| 5,879,406 A * | 3/1999 | Lilley ........................ 623/22.15 |
| 5,893,889 A | 4/1999 | Harrington |
| 5,916,269 A * | 6/1999 | Serbousek et al. ......... 623/22.24 |
| 5,935,174 A | 8/1999 | Dye |
| 5,938,702 A | 8/1999 | Lopez et al. |
| 5,957,979 A | 9/1999 | Beckman et al. |
| 5,987,685 A * | 11/1999 | Lambert ......................... 15/121 |
| 5,989,294 A * | 11/1999 | Marlow ..................... 623/22.16 |
| 5,997,579 A | 12/1999 | Albrektsson et al. |
| 6,013,103 A | 1/2000 | Kaufman et al. |
| 6,042,293 A | 3/2000 | Maughan |
| 6,059,830 A | 5/2000 | Lippincott, III et al. |
| 6,080,195 A | 6/2000 | Colleran et al. |
| 6,096,083 A | 8/2000 | Keller et al. |
| 6,126,695 A | 10/2000 | Semlitsch |
| 6,146,421 A | 11/2000 | Gordon et al. |
| 6,162,252 A | 12/2000 | Kuras et al. |
| 6,179,874 B1 | 1/2001 | Cauthen |
| 6,190,415 B1 | 2/2001 | Cooke et al. |
| 6,203,576 B1 | 3/2001 | Afriat et al. |
| 6,206,929 B1 | 3/2001 | Ochoa et al. |
| 6,217,249 B1 * | 4/2001 | Merlo ............................. 403/90 |
| 6,231,264 B1 | 5/2001 | McLaughlin et al. |
| 6,299,646 B1 | 10/2001 | Chambat et al. |
| 6,364,910 B1 | 4/2002 | Shultz et al. |
| 6,368,350 B1 | 4/2002 | Erickson et al. |
| 6,375,682 B1 | 4/2002 | Fleischmann et al. |
| 6,425,921 B1 | 7/2002 | Grundei et al. |
| 6,494,916 B1 * | 12/2002 | Babalola et al. ............. 623/23.3 |
| 6,558,427 B2 | 5/2003 | Leclercq et al. |
| 6,660,040 B2 * | 12/2003 | Chan et al. ................. 623/22.21 |
| RE38,409 E | 1/2004 | Noiles |
| 6,719,800 B2 | 4/2004 | Meyers et al. |
| 6,740,117 B2 | 5/2004 | Ralph et al. |
| 6,740,118 B2 | 5/2004 | Eisermann et al. |
| 6,743,258 B1 | 6/2004 | Keller |
| 6,770,095 B2 | 8/2004 | Grinberg et al. |
| 6,866,685 B2 * | 3/2005 | Chan et al. ................. 623/22.21 |
| 6,875,235 B2 | 4/2005 | Ferree |
| 6,893,465 B2 | 5/2005 | Huang |
| 6,896,703 B2 | 5/2005 | Barbieri et al. |
| 6,942,701 B2 | 9/2005 | Taylor |
| 6,949,105 B2 | 9/2005 | Bryan et al. |
| 6,964,686 B2 | 11/2005 | Gordon |
| 6,972,039 B2 | 12/2005 | Metzger et al. |
| 6,981,989 B1 | 1/2006 | Fleischmann et al. |
| 6,981,991 B2 | 1/2006 | Ferree |
| 6,986,791 B1 | 1/2006 | Metzger |
| 7,001,433 B2 | 2/2006 | Songer et al. |
| 7,037,341 B2 | 5/2006 | Nowakowski |
| 7,060,099 B2 | 6/2006 | Carli et al. |
| 7,060,101 B2 | 6/2006 | O'Connor et al. |
| 7,066,963 B2 | 6/2006 | Naegerl |
| 7,083,650 B2 | 8/2006 | Moskowitz et al. |
| 7,083,651 B2 | 8/2006 | Diaz et al. |
| 7,083,652 B2 | 8/2006 | McCue et al. |
| 7,108,719 B2 | 9/2006 | Horber |
| 7,108,720 B2 | 9/2006 | Hanes |
| 7,121,755 B2 | 10/2006 | Schlapfer et al. |
| 7,153,325 B2 | 12/2006 | Kim et al. |
| 7,179,294 B2 | 2/2007 | Eisermann et al. |
| 7,214,243 B2 | 5/2007 | Taylor |
| 7,214,244 B2 | 5/2007 | Zubok et al. |

(56) References Cited

U.S. PATENT DOCUMENTS

| | | | |
|---|---|---|---|
| 7,250,060 B2 | 7/2007 | Trieu | |
| 7,270,679 B2 | 9/2007 | Istephanous et al. | |
| 7,276,082 B2 | 10/2007 | Zdeblick et al. | |
| 7,297,164 B2 | 11/2007 | Johnson et al. | |
| 7,309,363 B2 | 12/2007 | Dietz | |
| 7,326,250 B2 | 2/2008 | Beaurain et al. | |
| 7,326,252 B2 | 2/2008 | Otto et al. | |
| 7,338,529 B1 | 3/2008 | Higgins | |
| 7,407,513 B2 | 8/2008 | Alleyne et al. | |
| 7,442,211 B2 | 10/2008 | de Villiers et al. | |
| 7,465,320 B1 | 12/2008 | Kito et al. | |
| 7,468,076 B2 | 12/2008 | Zubok et al. | |
| 7,468,079 B2 | 12/2008 | Collier | |
| 7,470,287 B2 | 12/2008 | Tornier et al. | |
| 7,485,145 B2 | 2/2009 | Purcell | |
| 7,494,507 B2 | 2/2009 | Dixon et al. | |
| 7,531,002 B2 | 5/2009 | Sutton et al. | |
| 7,537,615 B2 | 5/2009 | Lemaire | |
| 7,550,009 B2 | 6/2009 | Arnin et al. | |
| 7,550,010 B2 | 6/2009 | Humphreys et al. | |
| 7,572,295 B2 | 8/2009 | Steinberg | |
| 7,572,296 B2 | 8/2009 | Scott et al. | |
| 7,578,848 B2 | 8/2009 | Albert et al. | |
| 7,582,115 B2 | 9/2009 | Weber | |
| 7,588,384 B2 | 9/2009 | Yokohara | |
| 7,611,653 B1 | 11/2009 | Elsner et al. | |
| 7,618,439 B2 | 11/2009 | Zubok et al. | |
| 7,618,459 B2 | 11/2009 | Justin et al. | |
| 7,621,956 B2 | 11/2009 | Paul et al. | |
| 7,655,041 B2 | 2/2010 | Clifford et al. | |
| 7,658,767 B2 | 2/2010 | Wyss | |
| 7,740,659 B2 | 6/2010 | Zarda et al. | |
| 7,758,645 B2 | 7/2010 | Studer | |
| 7,758,653 B2 | 7/2010 | Steinberg | |
| 7,776,085 B2 | 8/2010 | Bernero et al. | |
| 7,879,095 B2 | 2/2011 | Pisharodi | |
| 7,905,919 B2* | 3/2011 | Kellar et al. | 623/16.11 |
| 7,914,580 B2* | 3/2011 | Kellar et al. | 623/16.11 |
| 8,029,574 B2* | 10/2011 | Kellar et al. | 623/23.41 |
| 8,070,823 B2* | 12/2011 | Kellar et al. | 623/23.4 |
| 8,308,812 B2* | 11/2012 | Kellar et al. | 623/23.4 |
| 8,512,413 B2* | 8/2013 | Kellar et al. | 623/23.41 |
| 2002/0111682 A1 | 8/2002 | Ralph et al. | |
| 2002/0143402 A1 | 10/2002 | Steinberg | |
| 2003/0055500 A1 | 3/2003 | Fell et al. | |
| 2003/0081989 A1 | 5/2003 | Kondoh | |
| 2003/0114935 A1* | 6/2003 | Chan et al. | 623/22.21 |
| 2003/0191534 A1 | 10/2003 | Viart et al. | |
| 2003/0220691 A1 | 11/2003 | Songer et al. | |
| 2004/0010316 A1 | 1/2004 | William et al. | |
| 2004/0024460 A1 | 2/2004 | Ferree | |
| 2004/0034433 A1* | 2/2004 | Chan et al. | 623/23.39 |
| 2004/0073311 A1 | 4/2004 | Ferree | |
| 2004/0088052 A1* | 5/2004 | Dearnaley | 623/16.11 |
| 2004/0093087 A1 | 5/2004 | Ferree et al. | |
| 2004/0117021 A1 | 6/2004 | Biedermann et al. | |
| 2004/0143332 A1 | 7/2004 | Krueger et al. | |
| 2004/0143334 A1 | 7/2004 | Ferree | |
| 2004/0167626 A1 | 8/2004 | Geremakis et al. | |
| 2004/0167629 A1 | 8/2004 | Geremakis et al. | |
| 2004/0172021 A1 | 9/2004 | Khalili | |
| 2004/0215345 A1 | 10/2004 | Perrone, Jr. et al. | |
| 2004/0220674 A1 | 11/2004 | Pria et al. | |
| 2004/0260396 A1 | 12/2004 | Ferree et al. | |
| 2004/0267374 A1* | 12/2004 | Friedrichs | 623/22.15 |
| 2004/0267375 A1* | 12/2004 | Friedrichs | 623/22.18 |
| 2005/0004572 A1 | 1/2005 | Biedermann et al. | |
| 2005/0015152 A1 | 1/2005 | Sweeney | |
| 2005/0021145 A1 | 1/2005 | de Villiers et al. | |
| 2005/0038516 A1 | 2/2005 | Spoonamore | |
| 2005/0055101 A1 | 3/2005 | Sifneos | |
| 2005/0071007 A1 | 3/2005 | Malek | |
| 2005/0080488 A1 | 4/2005 | Schultz | |
| 2005/0113926 A1 | 5/2005 | Zucherman et al. | |
| 2005/0113931 A1 | 5/2005 | Horber | |
| 2005/0125065 A1 | 6/2005 | Zucherman et al. | |
| 2005/0143827 A1 | 6/2005 | Globerman et al. | |
| 2005/0165485 A1 | 7/2005 | Trieu | |
| 2005/0171604 A1 | 8/2005 | Michalow | |
| 2005/0171614 A1 | 8/2005 | Bacon | |
| 2005/0192674 A1 | 9/2005 | Ferree | |
| 2005/0197706 A1 | 9/2005 | Hovorka et al. | |
| 2005/0203626 A1 | 9/2005 | Sears et al. | |
| 2005/0216081 A1 | 9/2005 | Taylor | |
| 2005/0251261 A1 | 11/2005 | Peterman | |
| 2005/0251262 A1 | 11/2005 | De Villiers et al. | |
| 2005/0261776 A1 | 11/2005 | Taylor | |
| 2006/0020342 A1 | 1/2006 | Ferree et al. | |
| 2006/0025862 A1 | 2/2006 | Villiers et al. | |
| 2006/0041314 A1 | 2/2006 | Millard | |
| 2006/0064169 A1 | 3/2006 | Ferree | |
| 2006/0085076 A1 | 4/2006 | Krishna et al. | |
| 2006/0095135 A1 | 5/2006 | Kovacevic | |
| 2006/0129240 A1 | 6/2006 | Lessar et al. | |
| 2006/0136062 A1 | 6/2006 | DiNello et al. | |
| 2006/0178744 A1 | 8/2006 | de Villiers et al. | |
| 2006/0190079 A1 | 8/2006 | Istephanous et al. | |
| 2006/0200247 A1 | 9/2006 | Charrois | |
| 2006/0217809 A1 | 9/2006 | Albert et al. | |
| 2006/0235527 A1 | 10/2006 | Buettner-Janz et al. | |
| 2006/0241765 A1 | 10/2006 | Burn et al. | |
| 2006/0241766 A1 | 10/2006 | Felton et al. | |
| 2006/0259147 A1 | 11/2006 | Krishna et al. | |
| 2006/0259148 A1 | 11/2006 | Bar-Ziv | |
| 2006/0271200 A1* | 11/2006 | Greenlee | 623/22.16 |
| 2006/0293752 A1 | 12/2006 | Moumene et al. | |
| 2007/0021837 A1 | 1/2007 | Ashman | |
| 2007/0032875 A1 | 2/2007 | Blacklock et al. | |
| 2007/0032877 A1* | 2/2007 | Whiteside | 623/22.15 |
| 2007/0050032 A1 | 3/2007 | Gittings et al. | |
| 2007/0073405 A1 | 3/2007 | Verhulst et al. | |
| 2007/0073410 A1 | 3/2007 | Raugel | |
| 2007/0083267 A1 | 4/2007 | Miz et al. | |
| 2007/0100447 A1 | 5/2007 | Steinberg | |
| 2007/0100454 A1 | 5/2007 | Burgess et al. | |
| 2007/0100456 A1 | 5/2007 | Dooris et al. | |
| 2007/0106391 A1* | 5/2007 | Ronk | 623/22.21 |
| 2007/0118223 A1 | 5/2007 | Allard et al. | |
| 2007/0123990 A1 | 5/2007 | Sharifi-Mehr | |
| 2007/0156246 A1 | 7/2007 | Meswania et al. | |
| 2007/0168037 A1 | 7/2007 | Posnick | |
| 2007/0173936 A1 | 7/2007 | Hester et al. | |
| 2007/0185578 A1 | 8/2007 | O'Neil et al. | |
| 2007/0208427 A1* | 9/2007 | Davidson et al. | 623/22.15 |
| 2007/0213821 A1 | 9/2007 | Kwak et al. | |
| 2007/0225806 A1 | 9/2007 | Squires et al. | |
| 2007/0225810 A1 | 9/2007 | Colleran et al. | |
| 2007/0225818 A1 | 9/2007 | Reubelt et al. | |
| 2007/0233244 A1 | 10/2007 | Lopez et al. | |
| 2007/0239276 A1 | 10/2007 | Squires et al. | |
| 2008/0065211 A1 | 3/2008 | Albert et al. | |
| 2008/0065216 A1 | 3/2008 | Hurlbert et al. | |
| 2008/0071381 A1* | 3/2008 | Buscher et al. | 623/18.11 |
| 2008/0077137 A1 | 3/2008 | Balderston | |
| 2008/0133017 A1 | 6/2008 | Beyar et al. | |
| 2008/0154263 A1 | 6/2008 | Janowski et al. | |
| 2008/0154369 A1 | 6/2008 | Barr et al. | |
| 2008/0161924 A1 | 7/2008 | Viker | |
| 2008/0161930 A1 | 7/2008 | Carls et al. | |
| 2008/0195212 A1 | 8/2008 | Nguyen et al. | |
| 2008/0215156 A1 | 9/2008 | Duggal et al. | |
| 2008/0221689 A1 | 9/2008 | Chaput et al. | |
| 2008/0221690 A1 | 9/2008 | Chaput et al. | |
| 2008/0228276 A1 | 9/2008 | Mathews et al. | |
| 2008/0228282 A1 | 9/2008 | Brodowski | |
| 2008/0243253 A1 | 10/2008 | Levieux | |
| 2008/0243262 A1 | 10/2008 | Lee | |
| 2008/0243263 A1 | 10/2008 | Lee et al. | |
| 2008/0300685 A1 | 12/2008 | Carls et al. | |
| 2009/0005872 A1 | 1/2009 | Moumene et al. | |
| 2009/0012619 A1 | 1/2009 | Cordaro et al. | |
| 2009/0030521 A1 | 1/2009 | Lee et al. | |
| 2009/0036992 A1 | 2/2009 | Tsakonas | |
| 2009/0043391 A1 | 2/2009 | de Villiers et al. | |

(56) References Cited

U.S. PATENT DOCUMENTS

| | | |
|---|---|---|
| 2009/0054986 A1 | 2/2009 | Cordaro et al. |
| 2009/0062920 A1 | 3/2009 | Tauber |
| 2009/0076614 A1 | 3/2009 | Arramon |
| 2009/0082867 A1 | 3/2009 | Sebastian Bueno et al. |
| 2009/0082873 A1 | 3/2009 | Hazebrouck et al. |
| 2009/0088865 A1 | 4/2009 | Brehm |
| 2009/0105758 A1 | 4/2009 | Gimbel et al. |
| 2009/0125111 A1 | 5/2009 | Copf, Jr. |
| 2009/0138090 A1 | 5/2009 | Hurlbert et al. |
| 2009/0157185 A1 | 6/2009 | Kim |
| 2009/0192616 A1 | 7/2009 | Zielinski |
| 2009/0192617 A1 | 7/2009 | Arramon et al. |
| 2009/0215111 A1 | 8/2009 | Veenstra et al. |
| 2009/0234458 A1 | 9/2009 | de Villiers et al. |
| 2009/0248161 A1 | 10/2009 | Theofilos et al. |
| 2009/0270986 A1 | 10/2009 | Christensen |
| 2009/0276051 A1 | 11/2009 | Arramon et al. |
| 2009/0281629 A1 | 11/2009 | Roebling et al. |
| 2009/0306784 A1 | 12/2009 | Blum |
| 2009/0306785 A1 | 12/2009 | Farrar et al. |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0004746 A1 | 1/2010 | Arramon |
| 2010/0030335 A1 | 2/2010 | Arramon |
| 2010/0063589 A1 | 3/2010 | Tepic |
| 2010/0063597 A1 | 3/2010 | Gradel |
| 2010/0100189 A1 | 4/2010 | Metzger |
| 2010/0100191 A1 | 4/2010 | May et al. |
| 2010/0161064 A1 | 6/2010 | Kellar et al. |
| 2010/0161072 A1 | 6/2010 | Drescher |
| 2010/0191342 A1 | 7/2010 | Byrd et al. |
| 2010/0262250 A1 | 10/2010 | Kellar et al. |
| 2010/0268340 A1 | 10/2010 | Capote et al. |
| 2010/0292794 A1 | 11/2010 | Metz-Stavenhagen |
| 2010/0331993 A1 | 12/2010 | Gradl |

FOREIGN PATENT DOCUMENTS

| | | |
|---|---|---|
| DE | 10164328 | 7/2003 |
| DE | 202008004709 | 7/2008 |
| EP | 46926 | 3/1982 |
| EP | 0636353 | 2/1995 |
| EP | 648478 | 4/1995 |
| EP | 1508315 | 2/2005 |
| FR | 2750036 | 12/1997 |
| FR | 2805456 | 8/2001 |
| FR | 2897528 | 8/2007 |
| GB | 1322680 | 7/1973 |
| GB | 1417407 | 12/1975 |
| GB | 1528906 | 10/1978 |
| GB | 2191402 | 12/1987 |
| JP | 2004011782 | 1/2004 |
| JP | 2004169820 | 6/2004 |
| WO | 9523566 | 9/1995 |
| WO | 9604867 | 2/1996 |
| WO | 97/16138 A1 | 5/1997 |
| WO | 97/38650 A1 | 10/1997 |
| WO | 9738650 | 10/1997 |
| WO | 0023015 | 4/2000 |
| WO | 03049649 | 6/2003 |
| WO | 2004066882 | 8/2004 |
| WO | 2005039455 | 5/2005 |
| WO | 2006/069465 A1 | 7/2006 |
| WO | 2007087730 | 8/2007 |
| WO | 2008088777 | 7/2008 |
| WO | 2008094260 | 8/2008 |
| WO | 2009094477 | 7/2009 |
| WO | 2009105884 | 9/2009 |
| WO | 2009121450 | 10/2009 |
| WO | 2009126908 | 10/2009 |
| WO | 2010095125 | 8/2010 |
| WO | 2011011340 | 1/2011 |

OTHER PUBLICATIONS

Wang, W., Wang, F., Jin, Z., Dowson, D., Hu, Y., "Numerical Lubrication Simulation of Metal-on-Metal Artificial Hip Joint Replacements: Ball-in-Socket Model and Ball-on-Plane Model", vol. 223 Part J, 2009, pp. 1073-1082, "Journal Engineering Tribology", [online] [retrieved Mar. 28, 2011].

Wang, F., Jin, Z., "Effect of Non-Spherical Bearing Geometry on Transient Elastohydrodynamic Lubrication in Metal-on-Metal Hip Joint Replacements", vol. 221, Part J, 2007, pp. 379-389, "Journal of Engineering Tribology", [online] [retrieved Mar. 28, 2011].

Wang, F., Brockett, C., Williams, S., Udofia, I., Fisher, J., Jin, Z., "Lubrication and Friction Prediction in Metal-on-Metal Hip Implants", vol. 53, Jan. 2008, pp. 1277-1293, "Phys. Med. Biol.", United Kingdom.

Clarke, I., "Role of Ceramic Implants: Design and Clinical Success with Total Hip Prosthetic Ceramic-to-Ceramic Bearings", No. 282, Sep. 1992, pp. 19-30, "Clinical Orthopeadics and Related Research", Kinamed, Inc., Newbury Park, California.

Gardelin, P., Seminario, J., Corradini, C., Fenollosa Gomez, J., "Total Hip Prostheses with Cup and Ball in Ceramic and Metal Sockets", vols. 192-195, 2001, pp. 983-988, "Key Engineering Materials", Trans Tech Publications, Switzerland.

Bruckmann, H., Keuscher, G., Huttinger, K., "Carbon, A Promising Material in Endoprosthetics. Part 2: Tribological Properties", vol. 1, Apr. 1980, pp. 73-81, "Biomaterials", IPC Business Press, West Germany.

Jalali-Vahid, D., Jagatia, M., Jin, Z., Dowson, D., "Prediction of Lubricating Film Thickness in UHMWPE Hip Joint Replacements", vol. 34, 2001, pp. 261-266, "Journal of Biomechanics", Elsevier Science Ltd., United Kingdom.

Swanson, S., "The State of the Art in Joint Replacement, Part 2: Present Practice and Results", pp. 335-339, Nov. 1977, "Journal of Medical Engineering and Technology", London, United Kingdom.

Kellar et al.; U.S. Appl. No. 12/983,191, filed Dec. 31, 2010.

Kellar et al., U.S. Appl. No. 13/046,311, filed Mar. 11, 2011.

Kellar et al., U.S. Appl. No. 13/073,963, filed Mar. 28, 2011.

Faizan, Ahmad, Goel, Vijay K., Garfin, Steven R., Bono, Christopher M., Serhan, Hassan, Biyani, Ashok, Elgafy, Hossein, Krishna, Manoj, Friesem, Tai, "Do Design Variations in the Artificial Disc Influence Cervical Spine Biomechanics? A Finite Element Investigation", Engineering Center for Orthopaedic Research Exellence (E-CORE), Departments of Bioengineering and Orthopaedic Surgery, 5046 NI, MS 303, Colleges of Engineering and Medicine, University of Toledo, Toledo, Ohio 43606, USA, Published online: Nov. 21, 2009.

Post, Zachary D., Matar, Wadih Y., Van De Leur, Tim, Grossman, Eric L., Austin, Matthew S., "Mobile-Bearing Total Knee Arthroplasty", vol. 25, No. 6, 2010, pp. 998-1003, "Journal of Arthroplasty", Philadelphia, Pennsylvania.

Fregly, Benjamin, J., Bei, Yanhong, Sylvester, Mark E., "Experimental Evaluation of an Elastic Foundation Model to Predict Contact Pressures in Knee Replacements", vol. 36, No. 11, Nov. 2003, pp. 1659-1668, "Journal of Biomechanics", Gainesville, Florida.

Minns, R.J., Campbell, J., "The 'Sliding Meniscus' Knee Prosthesis: Design Concepts", vol. 8, No. 4, Oct. 1979, pp. 201-205, "Engineering in Medicine", London, England.

Strickland, M.A., Taylor, M., "In-Silico Wear Prediction for Knee Replacements—Methodology and Corroboration", vol. 42, No. 10, Jul. 2009, "Journal of Biomechanics", Southampton, United Kingdom.

Halloran, Jason P., Easley, Sarah K., Patrella, Anthony J., Rullkoetter, Paul J., "Comparison of Deformable and Elastic Foundation Finite Element Simulations for Predicting Knee Replacement Mechanics", vol. 127, No. 5, Oct. 2005, pp. 813-818, "Journal of Biomechanical Engineering", Denver, Colorado.

Guerinot, Alexandre, E., Magleby, Spencer, P. Howell, Larry L., "Preliminary Design Concepts for Compliant Mechanism Prosthetic

(56) References Cited

OTHER PUBLICATIONS

Knee Joints", vol. 2B, pp. 1103-1111, 2004, "Proceedings of the ASME Design Engineering Technical Conference", Provo, Utah.

Walker, Peter, S., Sathasivam, Shivani, "The Design of Guide Surfaces for Fixed-Bearing and Mobile-Bearing Knee Replacements", vol. 32, No. 1, pp. 27-34, Jan. 1999, "Journal of Biomechanics", Middlesex, United Kingdom.

Wenzel, S.A. and Shepherd, D.E.T., "Contact Stresses in Lumbar Total Disc Arthroplasty", vol. 17, No. 3, 2007, pp. 169-173, "Biomedical Materials and Engineering", Edgbaston, UK.

Clewlow, J.P., Pylios, T. and Shepherd, D.E.T., "Soft Layer Bearing Joins for Spine Arthroplasty", vol. 29, No. 10, Dec. 2008, pp. 1981-1985, "Materials and Design", Edgabaston, UK.

Parea, Philippe E., Chana, Frank W., Bhattacharyab, Sanghita and Goelb, Vijay K., "Surface Slide Track Mapping of Implants for Total Disc Arthroplasty", vol. 42, No. 2, Jan. 19, 2009, pp. 131-139, "Journal of Biomechanics", [online] [retrieved Feb. 19, 2010].

Dooris, Andrew P., Goel, Vijay K., Todd, Dwight T., Grosland, Nicole M., Wilder, David G., "Load Sharing in a Lumbar Motion Segment Implanted with an Artificial Disc Under Combined Sagittal Plane Loading", BED—vol. 42, 1999, pp. 277-278, American Society of Mechanical Engineers, Iowa City, Iowa.

* cited by examiner

US 9,005,306 B2

MEDICAL IMPLANTS WITH COMPLIANT WEAR-RESISTANT SURFACES

BACKGROUND OF THE INVENTION

This invention relates generally to medical implants, and more particularly to medical implants having wear resistant geometries and wear resistant thin films thereon.

Medical implants, such as knee, hip, and spine orthopedic replacement joints and other joints and implants have previously consisted primarily of a hard metal motion element that engages a polymer contact pad. This has usually been a high density high wear resistant polymer, for example Ultra-High Molecular Weight Polyethylene (UHMWPE), or other resilient material. The problem with this type of configuration is the polymer eventually begins to degrade due to the caustic nature of blood, the high impact load, and high load cycle. As the resilient member degrades, pieces of polymer may be liberated into the joint area, often causing accelerated wear, implant damage, and tissue inflammation and harm.

It is desirable to employ a design using a hard member on a hard member e.g. metals or ceramics), thus eliminating the polymer. Such a design is expected to have a longer service life. Extended implant life is important as it is now often required to revise or replace implants. Implant replacement is undesirable from a cost, inconvenience, patient health, and resource consumption standpoint.

Implant using two hard elements of conventional design will be, however, subject to rapid wear. First, a joint having one hard, rigid element on another will not be perfectly shaped to a nominal geometry. Such imperfections will result in points of high stress, thus causing localized wear. Furthermore, two hard elements would lack the resilient nature of a natural joint. Cartilage has a definite resilient property, absorbing shock and distributing periodic elevated loads. This in turn extends the life of a natural joint and reduces stress on neighboring support bone and tissue. If two rigid members are used, this ability to absorb the shock of an active lifestyle could be diminished. The rigid members would transmit the excessive shock to the implant to bone interface. Some cyclical load in these areas stimulates bone growth and strength; however, excessive loads or shock stress or impulse loading the bone-to-implant interface will result in localized bone mass loss, inflammation, and reduced support.

BRIEF SUMMARY OF THE INVENTION

These and other shortcomings of the prior art are addressed by the present invention, which according to one aspect provides a medical implant, including: a first member adapted to be implanted to bone and having a substantially rigid first contact surface; and a second member adapted to be implanted to bone and having a substantially rigid second contact surface which bears against the first contact surface so as to transfer load from one member to the other while allowing relative motion between the two members. At least one of the first and second contact surfaces is adapted to have resilient properties when placed under load.

According to another aspect of the invention, a medical implant includes: a first member adapted to be implanted to bone and having a substantially rigid, convex-curved first contact surface; and a second member adapted to be implanted to bone and having a substantially rigid, concave-curved second contact surface riding against the first contact surface. The second contact is adapted to bend elastically in at least one plane when placed under a preselected operating load.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
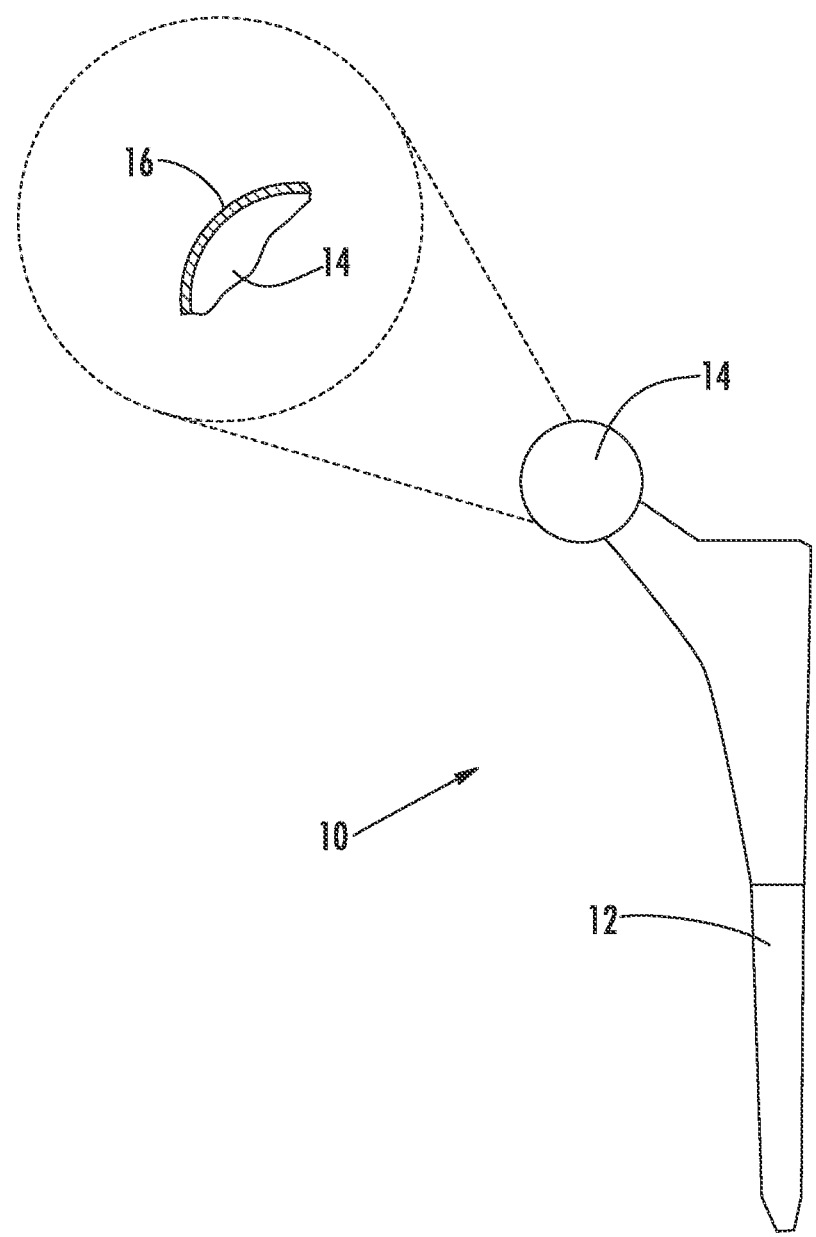
FIG. 1 is a side view of a lower portion of a hip implant constructed in accordance with the present invention.

Referring to the drawings wherein identical reference numerals denote the same elements throughout the various views, FIG. 1 depicts an exemplary lower member 10 of a hip implant constructed in accordance with the present invention. The lower member 10 is generally metallic and includes an elongated body 12 and a ball end 14. Although a hip implant is used as an example, the present invention is equally applicable to other types of implants The surface of the ball end 14, or portions thereof, has a thin film 16 of a carbon-based material deposited thereon, referred to as a diamond-like carbon (DLC) material. This thin film material is essentially pure carbon, has a noncrystalline microstructure, and exhibits a flexural capability of approximately 8% or better. The carbon structure and bond layer enable the thin film 16 to endure significant vibration and deformation without cracking or detaching from the substrate or delaminating. Such thin films may be obtained from BioMedFlex LLC, Huntsville, N.C., 28078.

The thin film 16 is applied in multiple layers, for example about 3 to about 30 layers may be used. The use of multilayers prevents residual stress build up in the individual layers and in the total film thickness This is in contrast to typical prior art thin films which have residual stress present and are brittle, limiting their ability to bear a localized load. The total thickness of the thin film 16 may be in the range of about 0.5 to about 6 μm. No post coating annealing or mechanical polishing is required, and the thin film 16 has a high adhesion strength, for example about 8500 lb/in$^2$ or greater.

Figure 2:
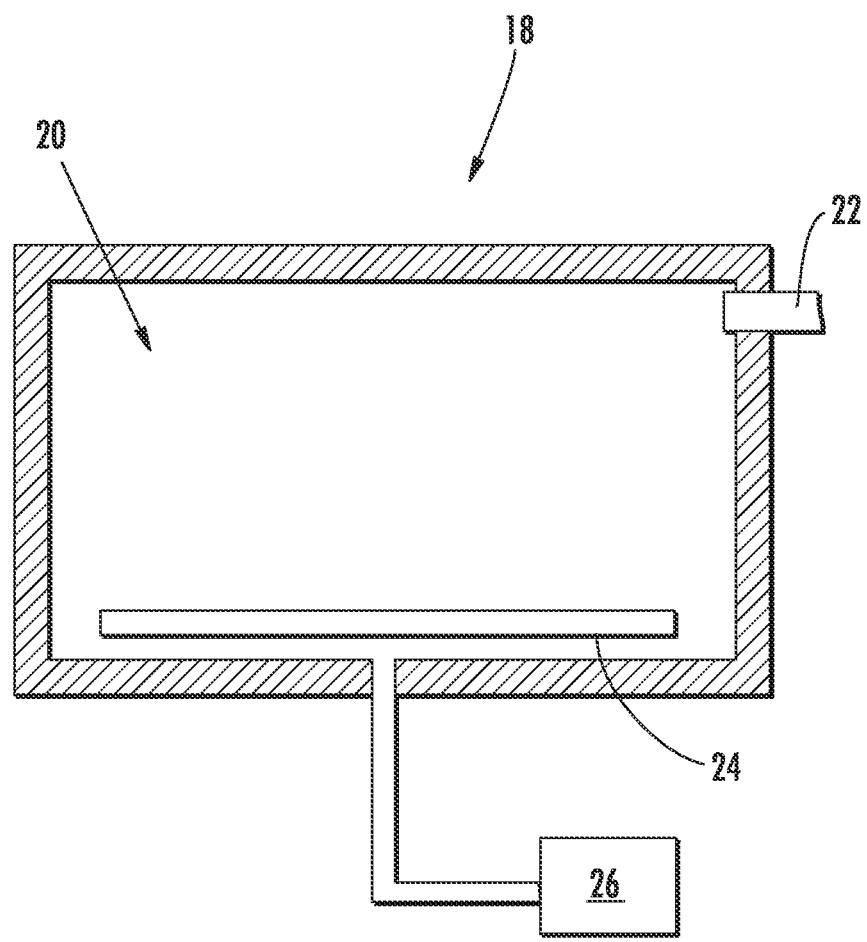
FIG. 2 is a schematic side view of a thin film treatment apparatus for use with the present invention.

FIG. 2 illustrates a thin film apparatus 18 for applying the thin film 16 to the lower member 10. The thin film apparatus 18 is a chemical vapor deposition (CVD) apparatus of a known type. It includes a processing chamber 20 which receives the workpiece, a hydrocarbon gas source 22, an RF field generator 24 of a known type, and a vacuum pump 26.

The thin film process proceeds as follows. First, the untreated lower member 10 is plasma cleaned in a known manner to eliminate any foreign material or contaminants from the surface thereof. The thin film 16 is then deposited over the exterior of the ball end 14 using a plasma assisted chemical vapor deposition (CVD) process. Since the thin film process is CVD, it does not require a direct line-of-sight to achieve a satisfactory thin film. Once the thin film cycle is complete, the lower member 10 is removed from the chamber 20.

It is also possible to construct the thin film 16 by alternating layers of metal doped DLC with layers of amorphous hydrogenated diamond like carbon. Examples of suitable materials for the multilayers include: amorphous hydrogenated carbon, silicon doped amorphous hydrogenated carbon, boron doped amorphous hydrogenated carbon, nitrogen doped amorphous hydrogenated carbon, boron nitride doped amorphous hydrogenated carbon, or other metal doped amorphous hydrogenated carbon.

The thin film 16 does not require an intermediate film or coating layer (such as TiN). It has a high electrical resistivity and high thermal conductivity. The thin film 16 may be doped with one or more metallic, semi-metallic or other elements to produce a balance of high hardness without sacrificing typical DLC coefficients of reduced friction, adhesion layer strength, and overall bond strength.

The thin film 16 has several beneficial effects to the surface on which it is applied. The thin film is conformal and more uniform than physical vapor deposition methods. It creates a non-porous, chemically inert, protective boundary layer. It improves the ability to withstand a localized (Hertzian) load while still providing exceptional wear resistance and high adhesion. It provides unique flexural property that allows the thin film 16 (and underlying substrate) to flex under load. This combination of flexural nature and high wear resistance makes the thin film 16 a solution for a variety of applications such as: gears (spiral bevel, hypoid, helical, spur, worm, etc.); medical implants; knees, hips, finger joint, spine, etc.; medical instruments; cams (and cam shafts) lifters (e.g. flat tappet); valves (automotive and industrial); curvic couplings; hurth couplings; bearings (e.g. gothic arch and planar and roller surface); shafts (especially shaft faces or shoulders); and other similar applications.

The thin film 16 has the ability to withstand scuffing and galling. It has a high hardness, low friction, and resists chemical wear. The thin film 16 enhances (fortifies) and protects the substrate surface to better preserve the exterior (exposed area) of the substrate to reduce the effects of micro surface damage (cracks and spalling); an initial wear indicator and mechanism. The high Hertzian contact stress tolerance makes it possible to actually maintain a hard carbon thin film 16 were prior art DLCs would fail (due to cracking and adhesion layer failure)

Superfinishing of the thin film 16 is possible. This would produce an even better surface finish on a processed surface than originally existed on the bare substrate; even if the original substrate was finished to a sub micron (<1 micro-inch Ra) surface finish.

Figure 3:
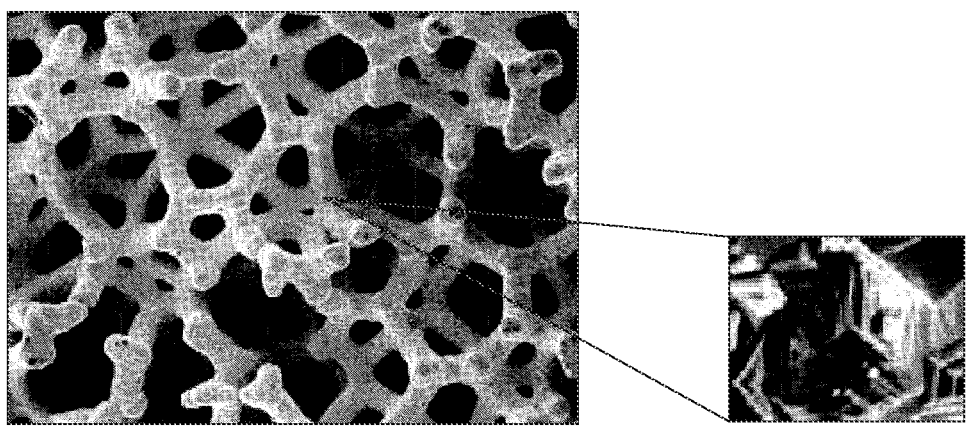
FIG. 3 is an enlarged view of a trabecular metal structure.

The resilient hard carbon thin film 16 described above may be used on implants having osseointegration surfaces, which are surfaces designed to be infiltrated by bone growth to improve the connection between the implant and the bone. Osseointegration surfaces may be made from materials such as trabecular metal, textured metal, or sintered or extruded implant integration textures. Trabecular metal is an open metal structure with a high porosity (e.g. about 80%). An example of a trabecular metal structure is shown in FIG. 3.

Figure 4:
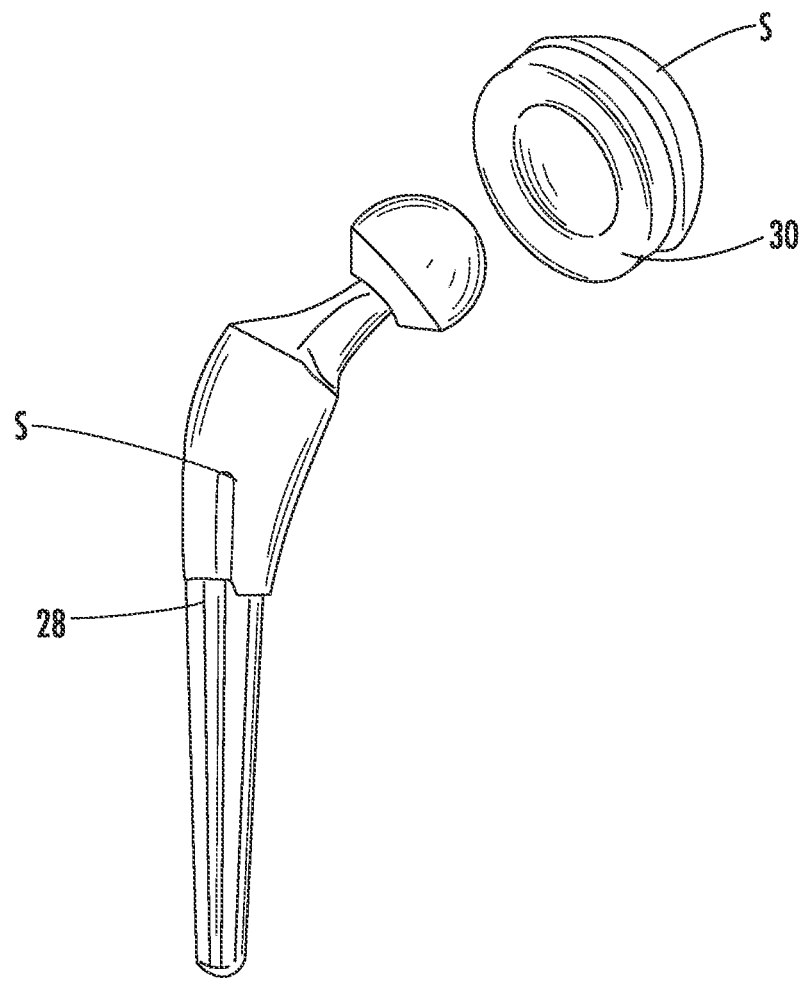
FIG. 4 is a perspective view of a hip implant.
Figure 5:
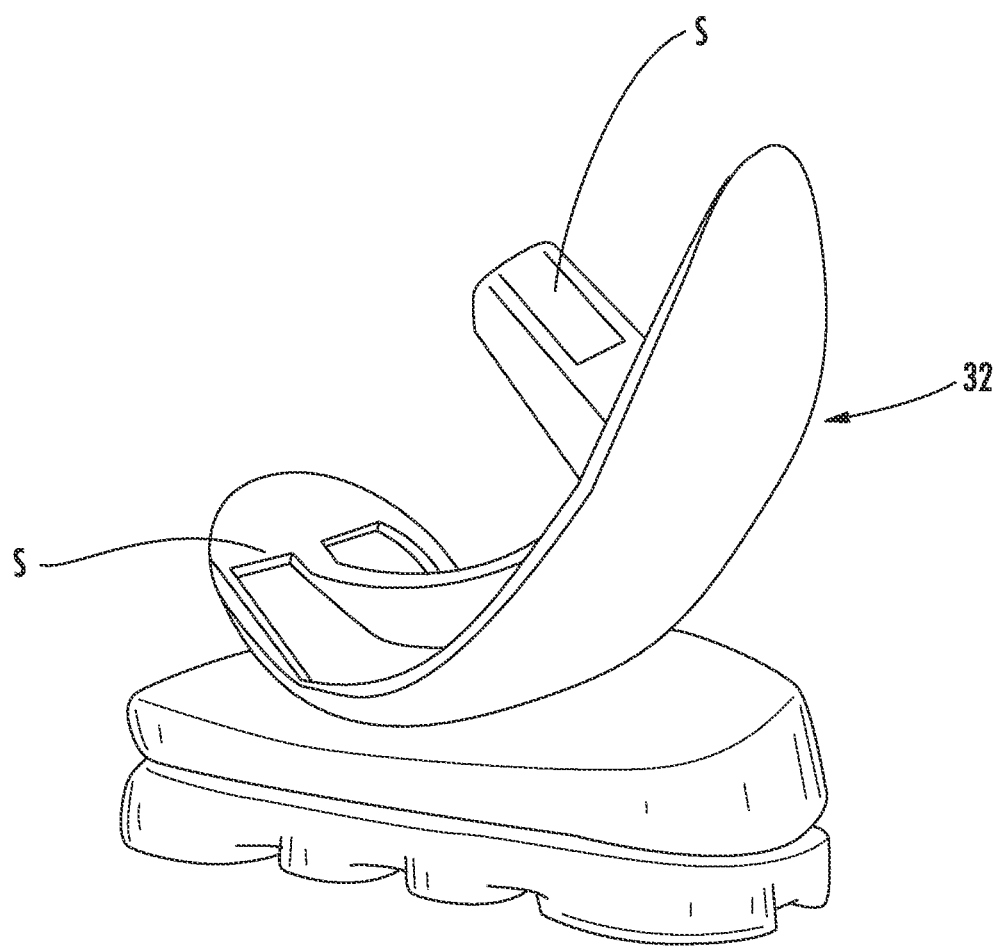
FIG. 5 is a perspective view of a portion of a knee implant.
Figure 6:
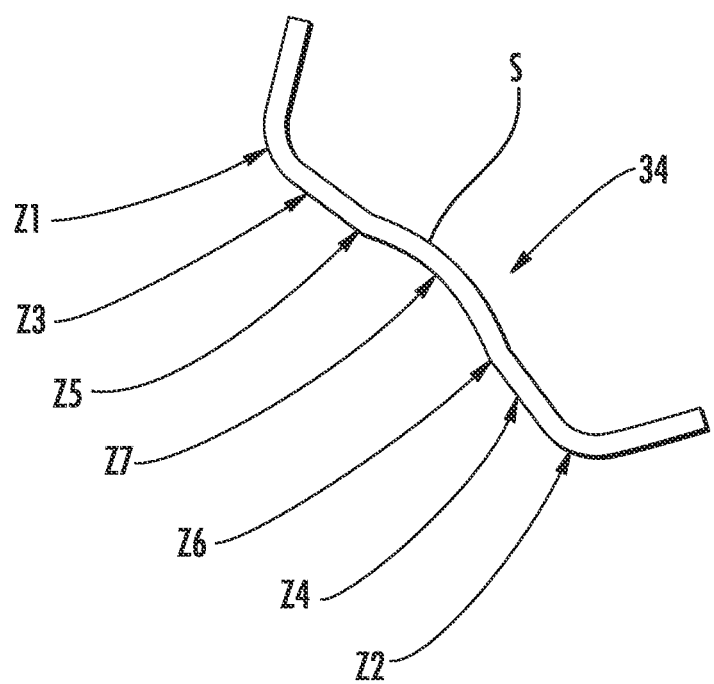
FIG. 6 is a cross-sectional view of a portion of a resilient contact member constructed in accordance with the present invention.

The thin film 16 may be applied to any osseointegration surface. FIGS. 4-6 illustrate various examples of implants having osseointegration surfaces "S", including a hip joint shank 28, a hip joint cup 30, and a knee joint 32. The thin film 16 may also be applied to other implants, such as plates and fasteners used for reconstructive procedures The thin film 16 may be doped to facilitate osseointegration, for example with titanium or fluorine. The thin film 16 may be a single layer of DLC material or a multilayer material as described above. If desired, a non-doped thin film may be used to create a wear resistant surface while discouraging bone integration. For example, in the hip joint lower member 10 of FIG. 2, the ball end 14 may be coated with a non-doped thin film 16 as described above.

In order to utilize the superior characteristics of the thin films described above, a specialized implant contact interface (implant geometry) may be used. In this geometry, an implanted joint would include two typically hard (i.e. metal or ceramic) members; however, at least one of the members is formed such that it has the characteristics of a resilient member, such as: the ability to absorb an impact load; the ability to absorb high cycle loading (high endurance limit); the ability to be self cleaning; and the ability to function as a hydrodynamic and/or hydrostatic bearing. One or both of these contact interface members may have thin film applied. If thin film is applied to two mating surfaces, it may be desirable to use two different compositions to improve the wear resistance and component compatibility. It may also be desired to apply thin film to one surface and a different surface treatment or coating to the mating surface.

Generally, the contact resilient member is flexible enough to allow elastic deformation and avoid localized load increases, but not so flexible as to risk plastic deformation, cracking and failure. In particular, the resilient member is designed such that the stress levels therein will be below the high-cycle fatigue endurance limit. As an example, the resilient member might be only about 10% to about 20% as stiff as a comparable solid member. It is also possible to construct the resilient member geometry with a variable stiffness, i.e. having a low effective spring rate for small deflections and a higher rate as the deflections increase, to avoid failure under sudden heavy loads.

FIG. 6 illustrates an exemplary contact member 34 including a basic resilient interface geometry. The contact member 34 is representative of a portion of a medical implant and is made of one or more metals or ceramics (for example, partially stabilized Zirconia). It is coated with a thin film (not shown) as described above. The geometry includes a lead in shape, Z1 and Z2, a contact shape, Z3 and Z4, a lead out shape, Z5 and Z6, and a relieved shape, Z7. It may be desired to vary the cross-sectional thickness to achieve a desired mechanical stiffness to substrate resilience characteristic. The presence of the relieved region Z7 introduces flexibility into the contact member 34, reduces the potential for concentrated point contact with a mating curved member, and provides a reservoir for a working fluid.

The Z7 region may be local to the contact member 34 or may be one of several. In any case, it may contain a means of providing fluid pressure to the internal contact cavity to produce a hydrostatic interface. A passive (powered by the regular motion of the patient) or active (powered by micro components and a dedicated subsystem) pumping means and optional filtration may be employed to provide the desired fluid interaction.

A hydrodynamic interface is desirable as, by definition, it means the contact member 34 is not actually touching the mating joint member. The lead-in and lead-out shapes Z1, Z2, Z5, Z6 are configured to generate a shear stress in the working fluid so as to create the fluid "wedge" of a hydrodynamic support. However, in this type of arrangement, there is a point where the two bearing surfaces are resting on each other in the absence of fluid shear between the two members of the joint or implant. This is what causes what is called stick-slip (the transition from static to dynamic friction then to hydrodynamic motion). The resilient nature of the thin film 16, allows a design which has reduced wear even when the contact member 34 flexes or is in a static friction regime.

Figure 7:
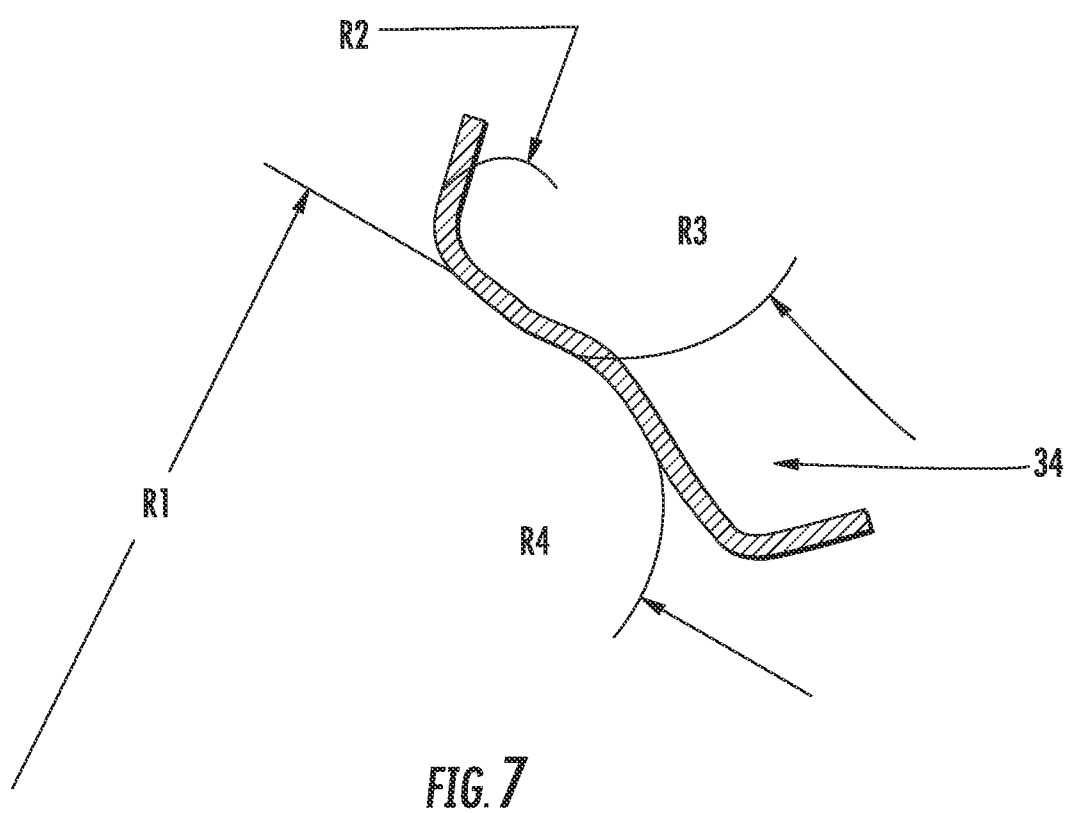
FIG. 7 is an enlarged view of the contact member of FIG. 7 in contact with a mating joint member.
Figure 8:
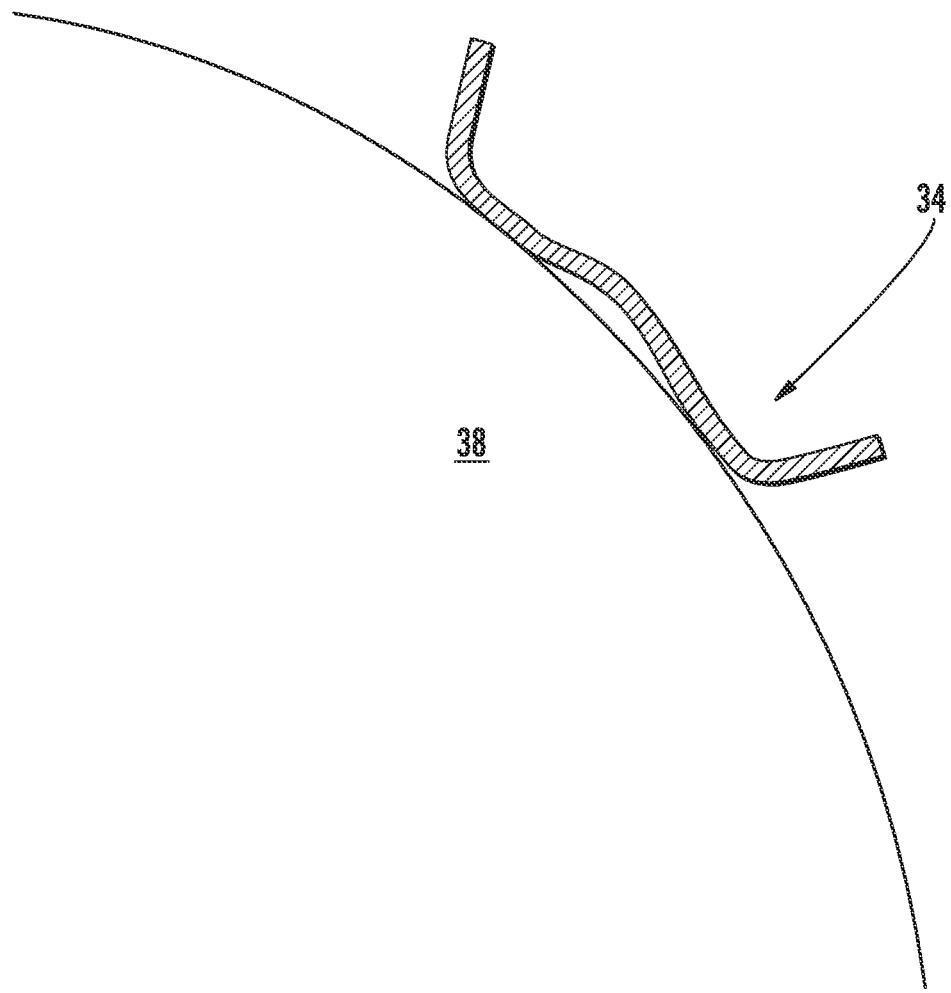
FIG. 8 is a side view of a resilient contact member in contact with a mating joint member.
Figures 9A, 9B:
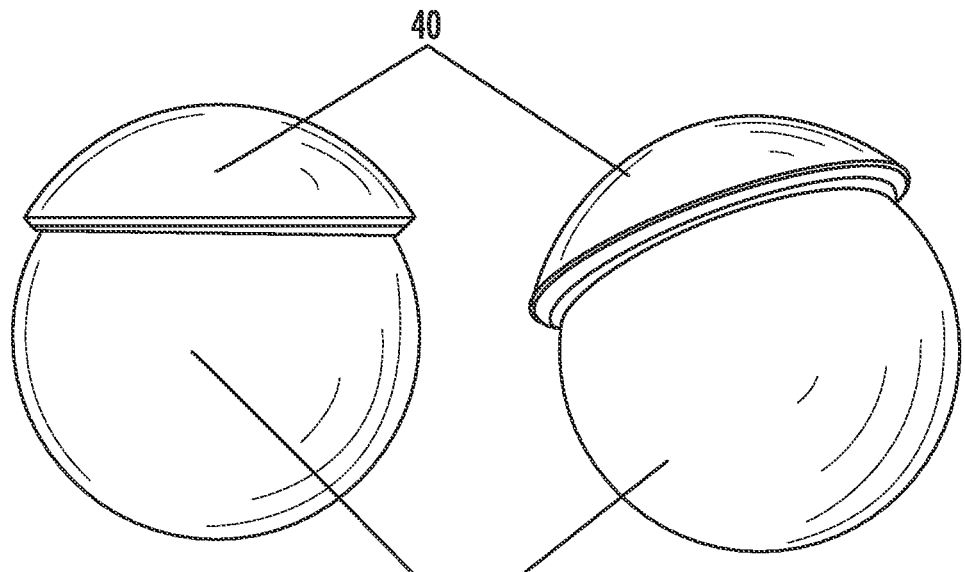
FIGS. 9A and 9B are side and perspective views, respectively, of a joint with mating members.
Figures 10A, 10B:
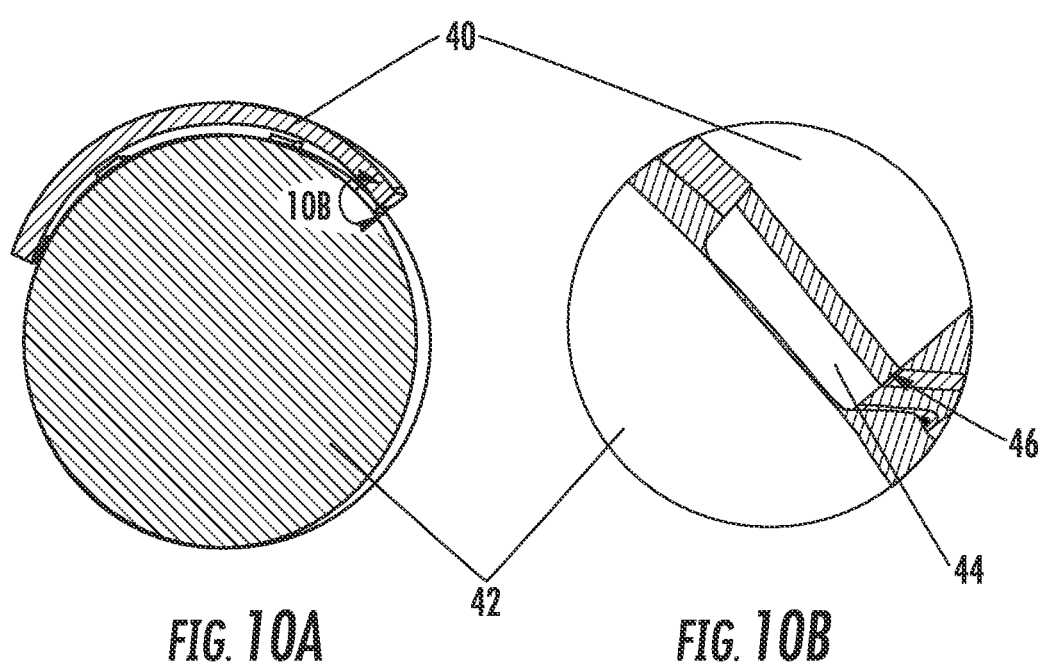
FIGS. 10A and 10B are overall and detailed cross-sectional views of the joint of FIGS. 9A and 9B.

FIG. 7 shows a closer view of the contact member 34. It may be desirable to make the contact radius (Z3 and Z4) larger or smaller, depending on the application requirement and flexural requirement. For example, FIG. 8 illustrates the contact member 34 in contact with a mating joint member 38 having a substantially larger radius than the contact member 34. The radius ratio between the two joint members is not particularly critical, so long as one of the members exhibits the resilient properties described herein.

Another way to achieve a resilient member is to employ a design that uses contacting surfaces with similar geometric relationships but sandwiches a resilient media between two semi-rigid elements. For example, FIGS. 9A-9B and 10A-10B illustrate a joint assembly with a cup 40 and a mating ball 42, both of generally rigid metals or ceramics. One or more ring-like rigid (i.e. metal or ceramic) contact pads 44 are attached to the cup 40, with a resilient material (e.g. polymer) 46 sandwiched between the two. In this case a polymer may be desirable as it is subjected to a distributed load versus the opportunity for localized wearing and degradation. The cup surface, including the contact pads 44, are coated with a thin film as described above.

Figure 11:
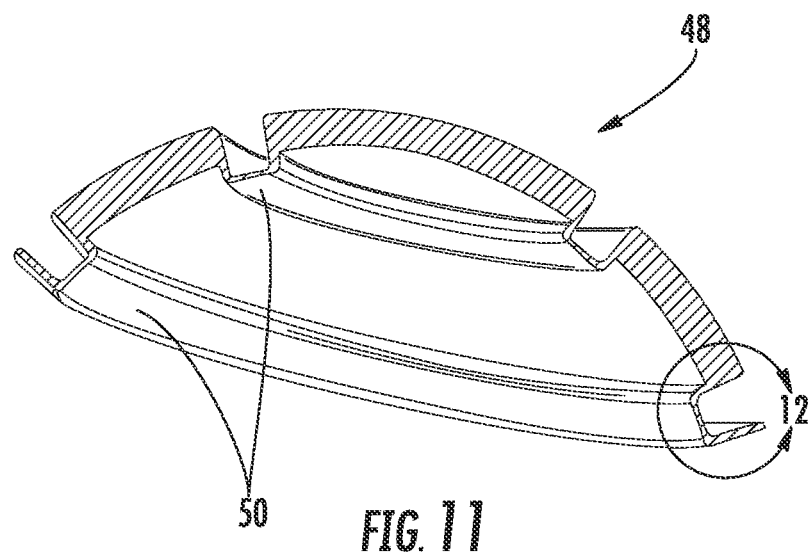
FIG. 11 is a cross-sectional view of a cup for an implant according to an alternate embodiment of the invention.
Figure 12:
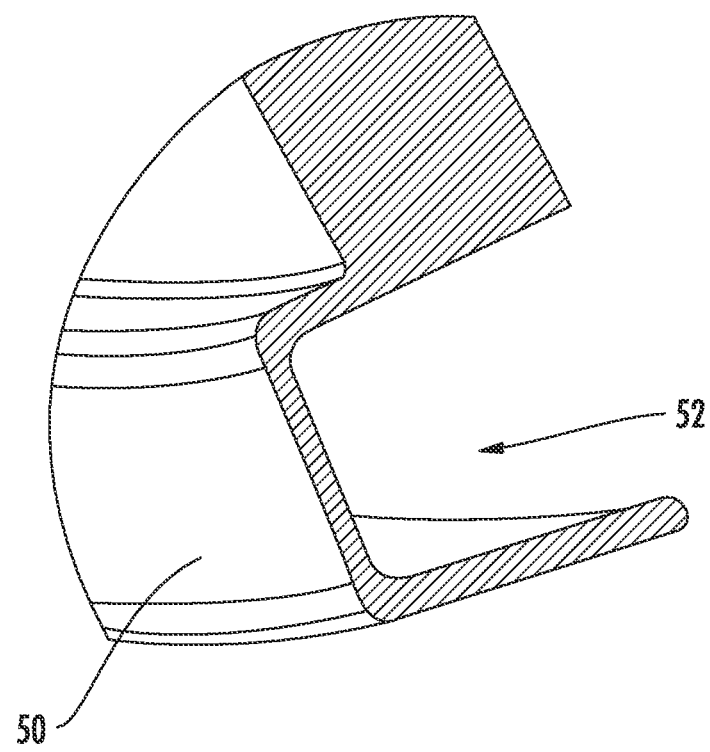
FIG. 12 is an enlarged view of a portion of the cup of FIG. 11.
Figures 13, 14:
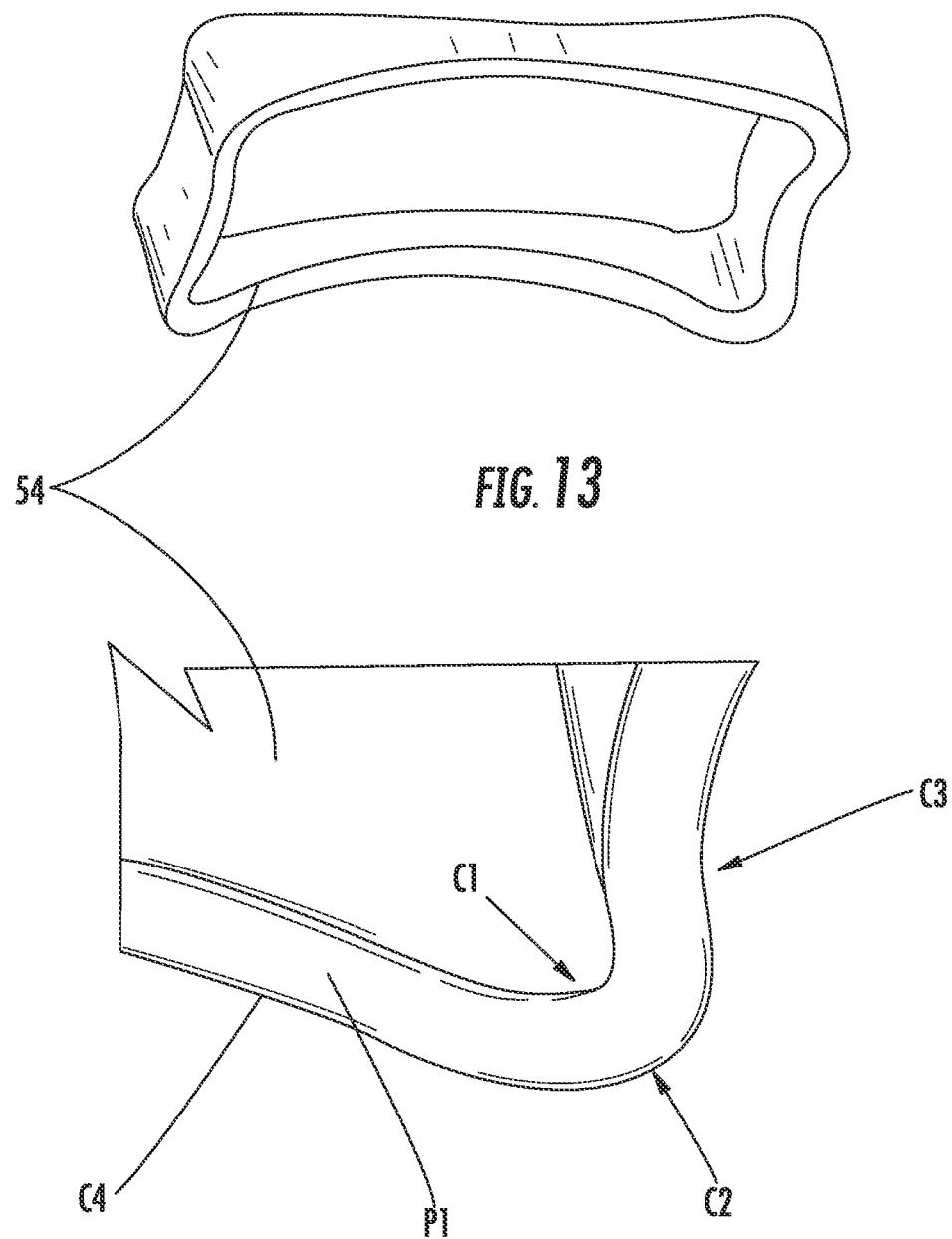
FIG. 13 is a perspective view of a segmented implant constructed according to the present invention.
FIG. 14 is an enlarged view of a portion of FIG. 13.
Figure 15D:
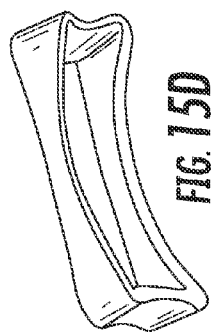
FIGS. 15A through 15C are various views of the implant of FIG. 13.
Figure 15B:
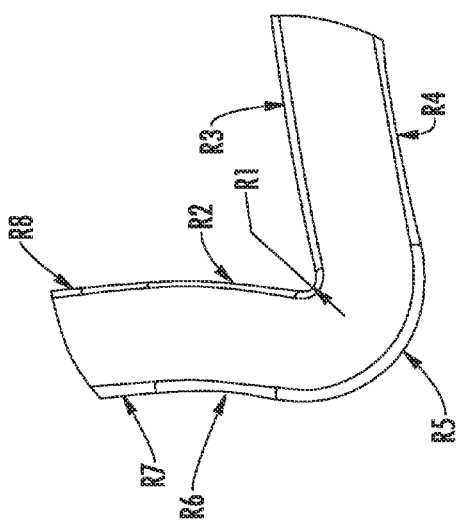
Figure 15A:
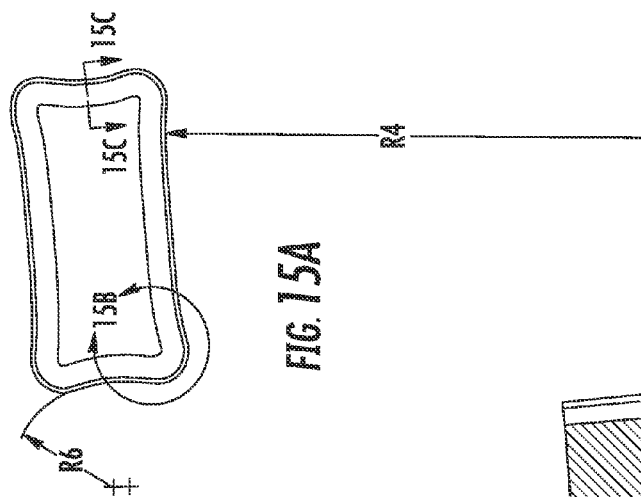
Figure 15C:
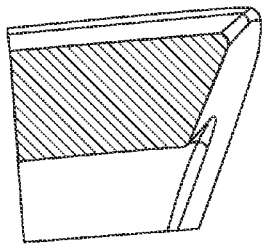
Figure 16C:
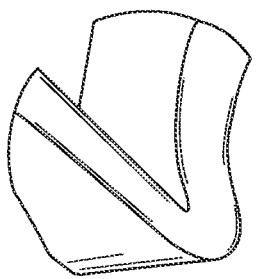
FIGS. 16A through 16F are various views of another segmented implant constructed according to the present invention.
Figure 16F:
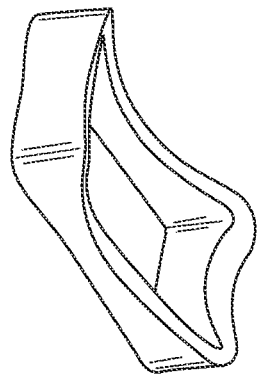
Figure 16B:
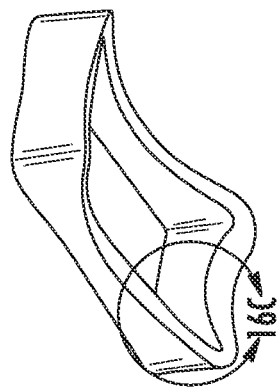
Figure 16E:
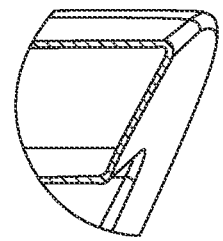
Figure 16A:
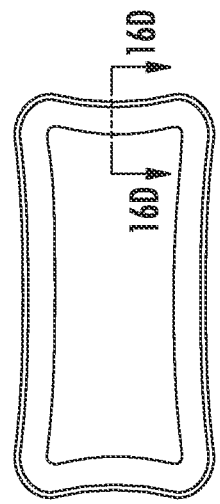
Figure 16D:
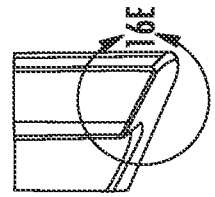
Figure 19:
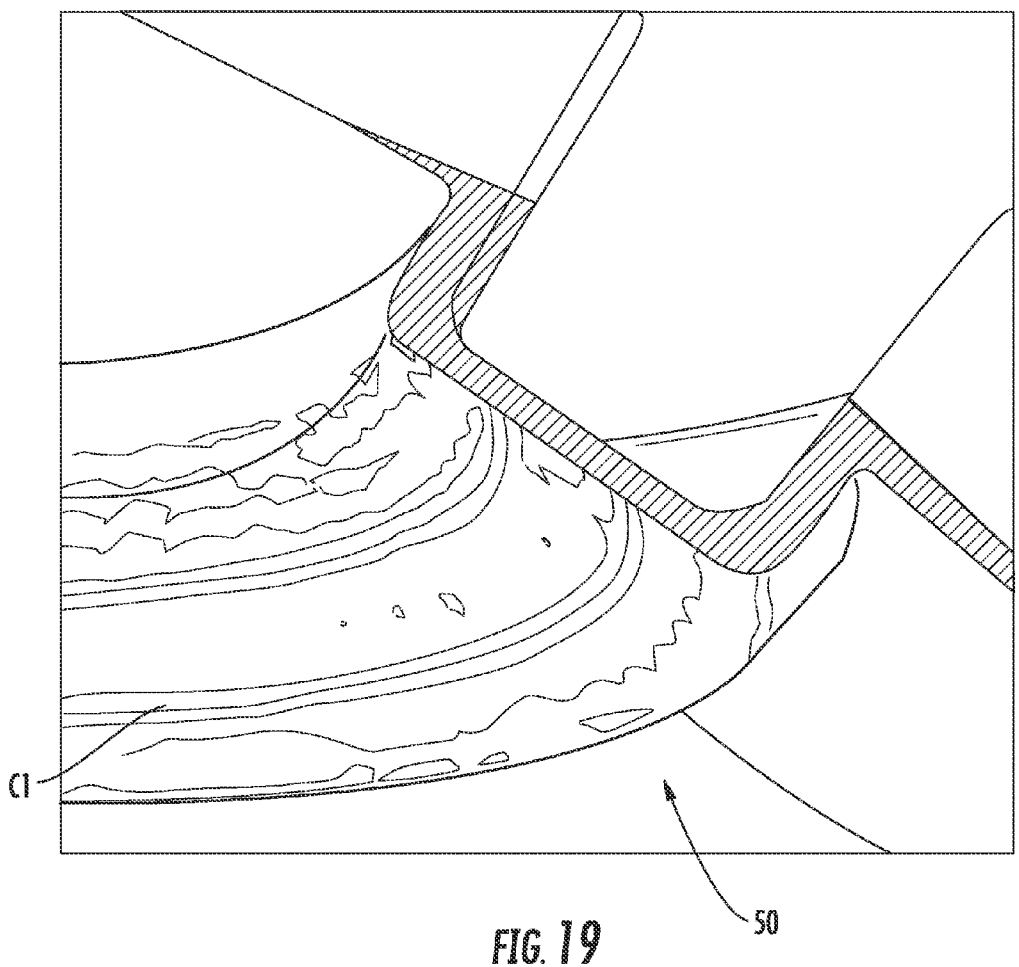
FIG. 19 is a perspective view of a finite element model of a joint member.

FIGS. 11 and 12 illustrate a coated cup 48 of metal or ceramic with two integrally-formed contact rings 50. More contact rings may be added if needed. As shown in FIG. 12, the volume behind the contact rings 50 may be relieved. This relieved area 52 may be shaped so as to produce a desired balance between resilience and stiffness. A varying cross-section geometry defined by varying inner and outer spline shapes may be desired. In other words, a constant thickness is not required. A material such as a gel or non-Newtonian fluid (not shown) may be disposed in the relieved area 52 to modify the stiffness and damping characteristics of the contact rings 50 as needed for a particular application. The cup 48 could be used as a stand-alone portion of a joint, or it could be positioned as a liner within a conventional liner. The contact ring 50 is shown under load in FIG. 19, which depicts contour lines of highest compressive stress at "C1". This is the portion of the contact ring 50 that would be expected to undergo bending first. The bearing interface portion of the resilient contact member could be constructed as a bridge cross-section supported on both sides as shown or as a cantilevered cross-section depending on the desired static and dynamic characteristics.

Figure 20:
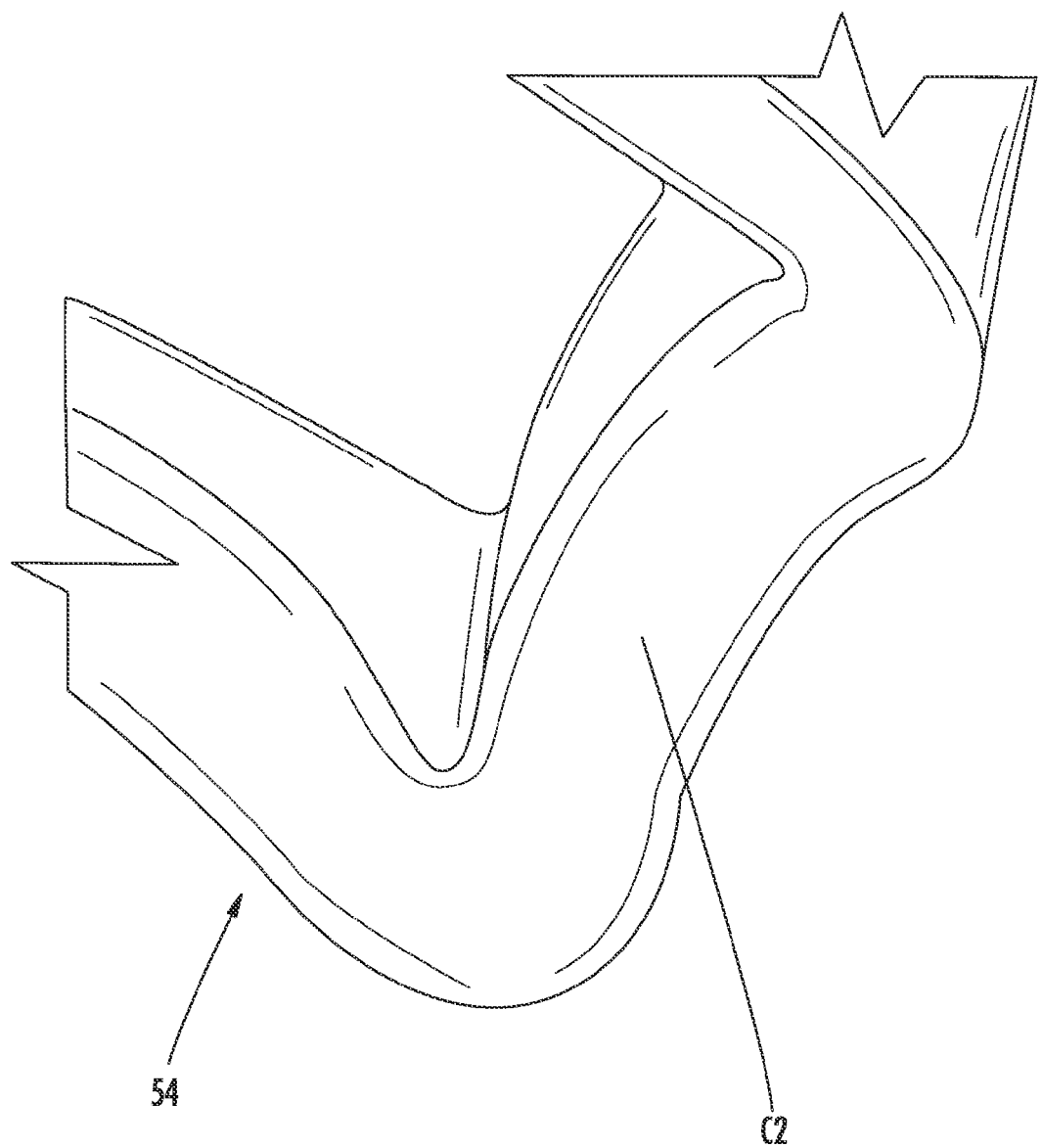
FIG. 20 is a perspective view of a finite element model of another joint member.

FIGS. 13-16 show a joint member 54 having a segmented shape. The generally rectangular shape (in plan view) is illustrative and could be modified to suit a specific requirement. Contours C1 and C2 and C3 and C4 can be shaped as needed to yield the desired contact area and profile and contour coverage. Contact profile P1 can be modified to suit the load and resilience characteristic desired for the specific application. The joint member 54 may be solid in the center zone or open. The contact surface can have shaped grooves (for example in the profile P1) positioned to allow particles to move off the load bearing contact surface and eventually move back into the joint for absorption back into the body. The joint member 54 is shown under load in FIG. 20, which depicts an area of highest compressive stress at "C2". This is the portion of the joint member 54 that would be expected to undergo bending first.

Figure 17:
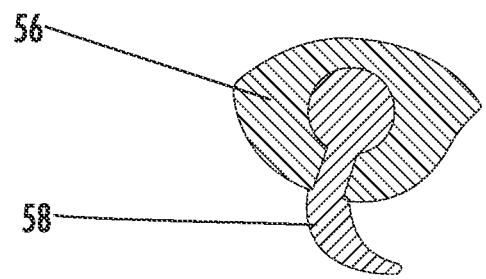
FIG. 17 is a cross-sectional view of an implant joint including a flexible seal.
Figure 18:
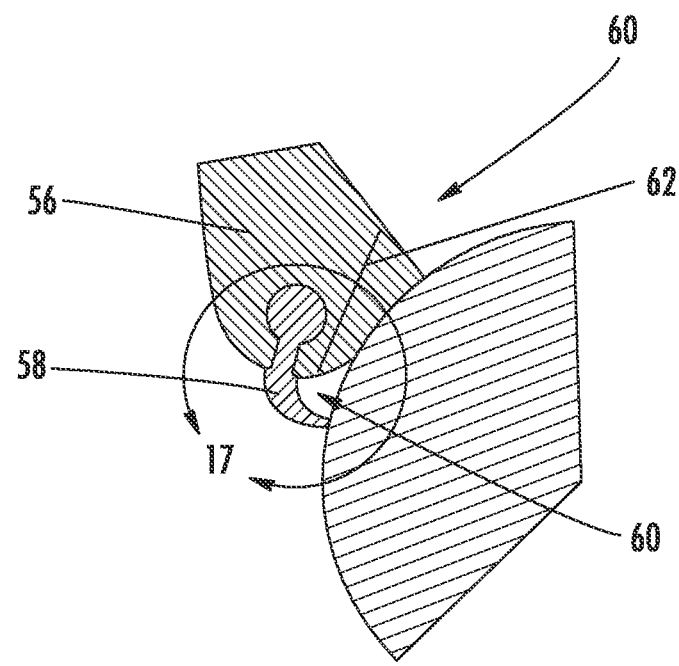
FIG. 18 is an enlarged view of a portion of FIG. 17.

FIGS. 17 and 18 illustrate an implant 56 of rigid material which includes a wiper seal 58. The wiper seal 58 keeps particles out of the contact area (seal void) 60 of the implant 58, and working fluid (natural or synthetic) in. The seal geometry is intended to be representative and a variety of seal characteristics may be employed; such as a single lip seal, a double or multiple lip seal, a pad or wiper seal made from a variety of material options. Different seal mounting options may be used; lobe in shaped groove as shown in FIGS. 17 and 18, a retaining ring or clamp, adhesion substance. The seal may also be incorporated into the contact face of the interface zone.

It may be desirable to create a return passage 62 from the seal void region 60 back into the internal zone 64 in order to stabilize the pressure between the two and to allow for retention of the Internal zone fluid if desired. This is especially relevant when the hydrostatic configuration is considered.

It is noted that it may be desirable to surface treat either or both interfaces of any of the above-described joints with a laser, shot peen, burnishing, or water shock process, to reduce wear. The benefit could be as much from surface annealing and microstructure and microfracture elimination as smoothing itself.

The foregoing has described medical implants with wear-resistant geometries and coatings. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A prosthetic joint implant, comprising:
    a first member having a concave interior, the first member adapted to be implanted into a first bone of a joint of a patient and having a rigid first contact surface made of ceramic, metal, or a combination thereof, the first contact surface comprising a continuous surface which includes a cup surface and at least one continuous peripheral contact ring protruding from the cup surface and into the concave interior, the at least one continuous peripheral contact ring integral with the remainder of the first contact surface and made of ceramic, metal, or a combination thereof;
    a second member adapted to be implanted into a second bone of the joint of the patient and adapted to articulate with the first member when implanted, the second member having a rigid second contact surface made of ceramic, metal, or a combination thereof which bears against the at least one continuous peripheral contact ring so as to transfer load from one member to the other while allowing relative motion between the two members;

wherein the first member is sized and shaped such that the at least one continuous peripheral contact ring bends elastically in at least one plane when placed under loads exerted by the second member when implanted into the joint of the patient, so as to avoid localized load increases between the first and second contact surfaces and between the prosthetic joint implant and the first or second bone.

2. The prosthetic joint implant of claim 1 wherein a resilient carbon-based thin film is disposed on at least one of the contact surfaces, the thin film consisting essentially of carbon in a non-crystalline microstructure.

3. The prosthetic joint implant of claim 1, wherein a volume behind the at least one continuous peripheral contact ring is hollow.

4. The prosthetic joint implant of claim 3, wherein a fluid is disposed in the volume behind the at least one continuous peripheral contact ring.

5. The prosthetic joint implant of claim 1 wherein a selected one of the first and second contact surfaces carries a resilient wiper seal which bears against the other one of the contact surfaces.

* * * * *